United States Patent [19]

Smith

[11] Patent Number: 4,700,833
[45] Date of Patent: Oct. 20, 1987

[54] SUTURE WINDING CARD

[75] Inventor: Andrea Smith, Shillington, Pa.

[73] Assignee: Sharpoint L.P., Reading, Pa.

[21] Appl. No.: 827,358

[22] Filed: Feb. 7, 1986

[51] Int. Cl.[4] .................... A61B 17/04; A61L 17/00
[52] U.S. Cl. .................... 206/380; 206/63.3; 206/388; 206/227; 206/492; 229/87.5
[58] Field of Search ............ 206/63.3, 381, 382, 206/380, 388, 227, 482, 492; 229/87.5, 72

[56] References Cited

U.S. PATENT DOCUMENTS

| D. 268,811 | 5/1983 | Black | D9/303 |
|---|---|---|---|
| 863,724 | 8/1907 | King | 229/72 |
| 1,131,135 | 3/1915 | Hudson | 229/87.5 |
| 1,444,497 | 2/1923 | Dickinson | 229/72 |
| 2,032,153 | 2/1936 | Schneider | 229/72 |
| 2,318,278 | 5/1943 | Arnold | 229/72 |
| 2,863,599 | 12/1958 | Whitman | 229/72 |
| 3,876,068 | 4/1975 | Sonnino | 206/227 |
| 4,253,563 | 3/1981 | Komarnycky | 206/63.3 |
| 4,412,614 | 11/1983 | Ivanov et al. | 206/63.3 |
| 4,427,109 | 1/1984 | Roshdy | 206/63.3 |
| 4,483,437 | 11/1984 | Cerwin et al. | 206/63.3 |
| 4,491,218 | 1/1985 | Aday | 206/63.3 |
| 4,496,045 | 1/1985 | Ferguson et al. | 206/63.3 |
| 4,555,016 | 11/1985 | Aday et al. | 206/63.3 |
| 4,574,948 | 3/1986 | Huck et al. | 206/380 |
| 4,574,957 | 3/1986 | Stead | 206/63.3 |

FOREIGN PATENT DOCUMENTS

207793  3/1909  Fed. Rep. of Germany ........ 229/72

Primary Examiner—Stephen Marcus
Assistant Examiner—Brenda J. Ehrhardt
Attorney, Agent, or Firm—William H. Elliott, Jr.; Richard D. Weber

[57] ABSTRACT

A suture winding card comprising a base panel and a plurality of flaps extending from and foldable over the base panel to cover and secure a suture thread coil disposed thereon. One of the flaps includes a plurality of triangularly shaped flap portions which can be selectively folded to form a pocket for receiving the end of a suture needle.

21 Claims, 15 Drawing Figures

SUTURE WINDING CARD

BACKGROUND OF THE INVENTION

1. Technical Field

The present invention relates generally to the packaging of surgical sutures and relates more particularly to a flat paper blank foldable to form a suture winding card adapted for the packaging of a number of types of sutures.

2. Background Information

The packaging of surgical sutures and surgical threads is complicated by the variety of types and sizes of sutures as well as surgical thread. The combination of a length of surgical thread with a needle attached to one or both ends thereof is known as a suture, and sutures are made with needles of various types and sizes and with surgical thread in a variety of sizes and lengths.

Since each suture or surgical thread package must maintain the sterility of the contents from the time of manufacture and packaging until the time of use, it is essential that the package be structured such that it will withstand transportation, storage and handling processes without jeopardizing the sterility of its contents. In the case of needles, provision must be made to prevent the inadvertent puncture of the package by the sharp needle point or edge, which would, of course, immediately compromise the sterility of the package.

In the past, a variety of packaging arrangements have been utilized for sutures and for surgical thread but, for the most part, these packages have been designed for a particular type of product, for example a suture including a long straight needle, or a suture having a small curved needle. The use of folded paper stock as the initial package element has been widely used in various configurations, with one or more additional sealed packaging elements enveloping the folded card bearing the suture or surgical thread to maintain the sterility of the contents.

Typically, the suture needle in conventional packages is secured to a paper carrier card by means of a slit in the card through which the needle is passed. Examples of such an arrangement are shown, for example, in U.S. Pat. Nos. Des. 268,811, 3,876,068 and 4,496,045. Such arrangements do not serve to positively anchor the needle in place, and needle migration could permit the needle point to penetrate the sealed package.

SUMMARY OF THE INVENTION

The present invention provides a suture winding card, the structure of which permits a variety of packaging uses for packaging different types of sutures or surgical thread, and which provides a needle pocket for effectively preventing wandering of the needle and penetration of the package. The invention comprises a flat paper blank having fold lines thereon permitting the folding of at least two flaps extending from a base panel, said base panel and said flaps being configured and having fold lines and slits to enable the attachment of sutures and surgical thread thereto as the initial stage in providing a sterile package.

The base panel of the blank includes a plurality of slits defining tabs which may be displaced therefrom to permit the winding of surgical thread therearound. The tabs are preferably located adjacent the corners of the rectangular base panel to permit a circular winding of thread therearound. The base panel also includes a pair of spaced apertures to receive pins of winding equipment around which surgical threads may be wound in the desired pattern, such as a figure eight pattern.

A first flap extending from the base panel includes a series of three fold lines converging at a common point at one end of the fold line of the flap connecting the flap to the base panel. These three fold lines define triangular flap portions which are foldable into several different needle receiving pockets depending upon the style of needle being packaged.

A second foldable flap having a fold line at right angles to the fold line of the first flap extends from its common fold line with the base panel completely across the base panel in its folded position and substantially covers the suture or thread disposed on the base panel. Means are provided for locking the second flap in a folded condition overlapping the base panel or first flap. The second flap is preferably provided with slits defining needle or thread securing apertures or tabs.

A third flap disposed opposite said first flap and a fourth flap disposed opposite said second flap may be provided in the blank, which third and fourth flaps when folded over said base panel in an appropriate sequence provide a complete containment of the suture or thread disposed on the base panel. Means may be provided to permit the latching of the cover panel to the second foldable panel to maintain the folded condition of the first, second, third and cover flaps.

It is accordingly a first object of the present invention to provide a suture packaging card which is adapted to the sterile packaging of a variety of types of sutures and surgical thread.

A further object of the invention is to provide a card as described which includes a flap having foldable portions which can be alternately folded to provide several types of needle pockets.

Another object of the invention is to provide a card as described which can be economically manufactured in the form of a flat paper blank.

Still another object of the invention is to provide a card as described which may be utilized in conjunction with automatic packaging machinery.

Additional objects and advantages of the invention will be more readily apparent from the following description of a preferred embodiment thereof.

DESCRIPTION OF THE PREFERRED EMBODIMENTS

Figure 1:
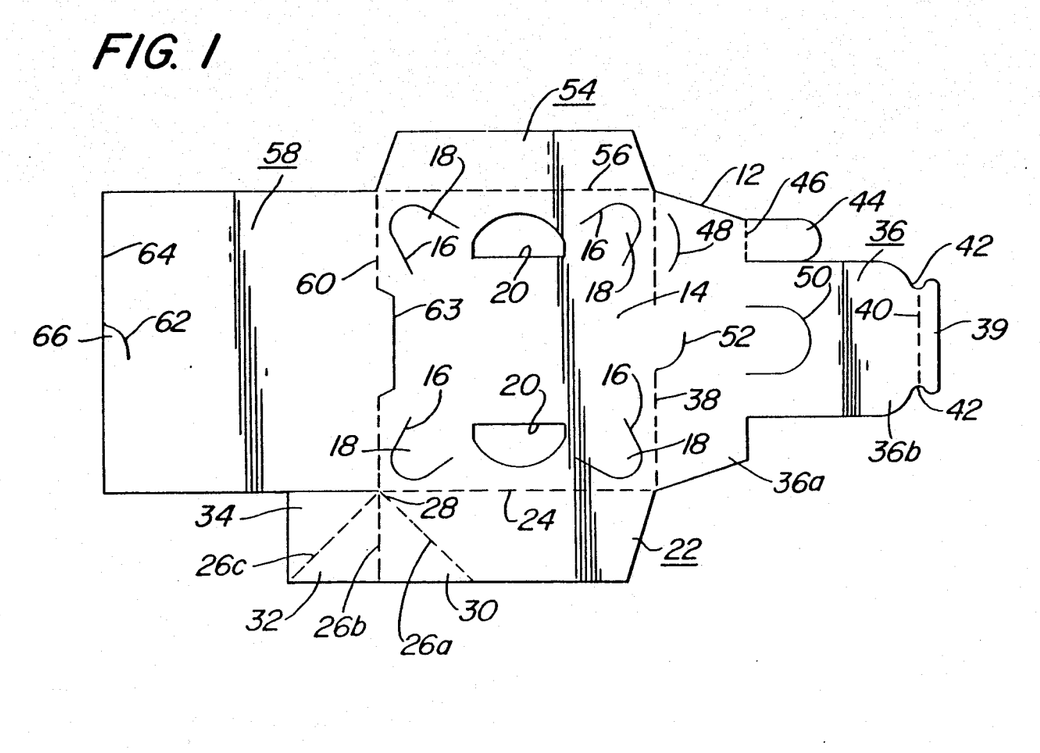
FIG. 1 is a plan view of a paper blank foldable into a preferred form of suture winding card in accordance with the present invention.

Referring to the drawings and particularly FIG. 1 thereof, a blank generally designated 12 is illustrated from which a suture winding card in accordance with the invention may be formed by folding a plurality of flaps along indicated fold lines.

The blank 12 includes a rectangular base panel 14 defined along its four edges by fold lines, each of which delineates a flap foldable over the base panel for purposes to be described. The base panel 14 is designed to receive a suture winding thereon. Such winding may be received or retained on the panel in several ways. For relatively stiff sutures, a plurality of U-shaped slits 16 are cut in the base panel in each corner thereof, each cut defining a tab 18 having its convex portion directed toward a panel corner. By a slight displacement of the tabs 18 away from the plane of the blank, the tabs may serve to receive a coiled length of surgical thread or suture in the manner shown for example in FIG. 2 or 9.

Figures 5, 6, 6A:
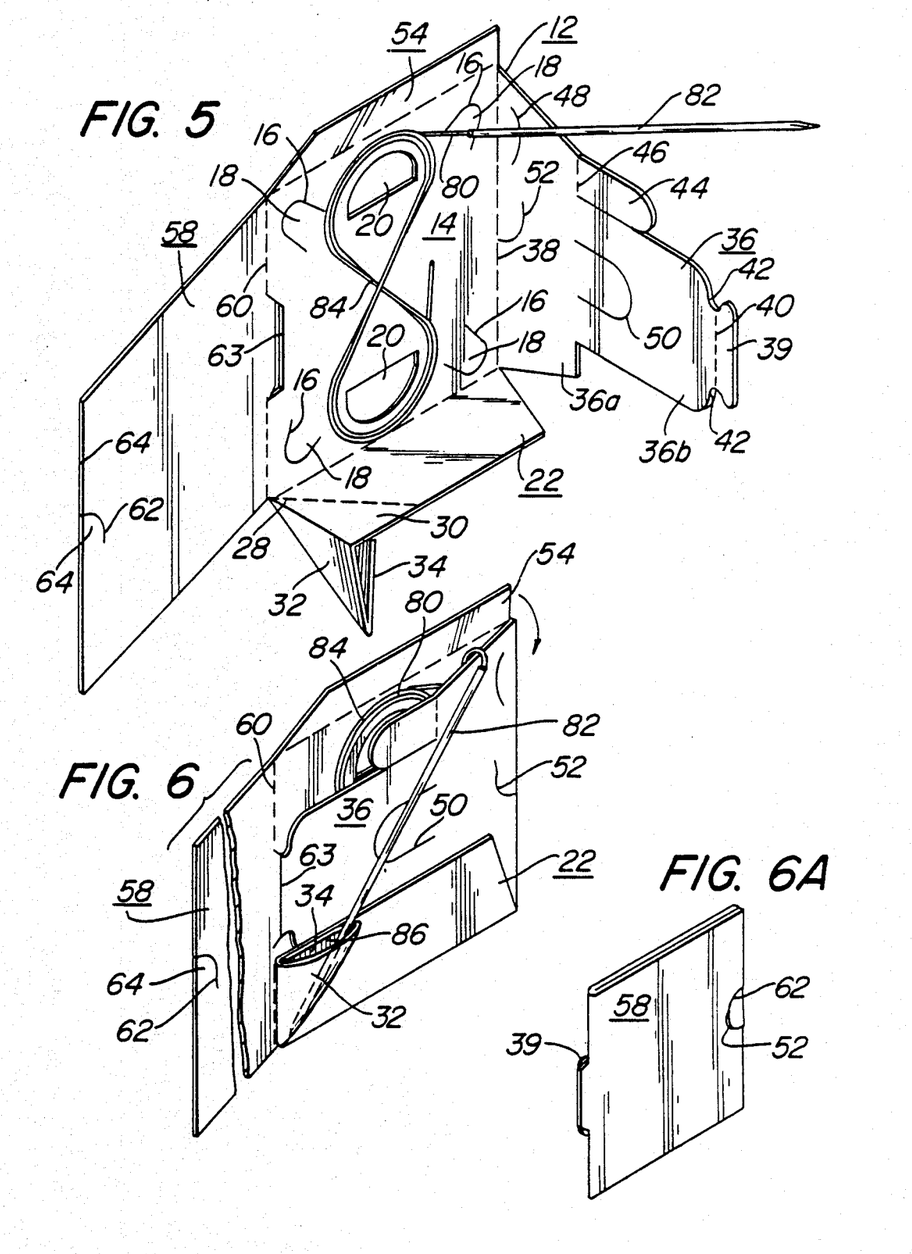
FIG. 5 is a perspective view of the blank of FIG. 1 partially folded and shown with a suture comprising a straight elongated needle in partially packaged disposition on the blank.
FIG. 6 is a view of the blank and suture of FIG. 5 with all of the flaps folded except for the cover flap.
FIG. 6A is a reduced perspective view of the suture package of FIGS. 5 and 6 with the cover flap closed.

The base panel 14 may also include a pair of opposed D-shaped apertures 20, which apertures are utilized to receive a pair of pins (not shown) around which surgical thread or a suture may be wound, such as in a figure eight pattern as shown in FIG. 5. The apertures 20 accordingly provide for an alternate arrangement for the winding of a length of thread on the card package.

Figures 2, 3, 4:
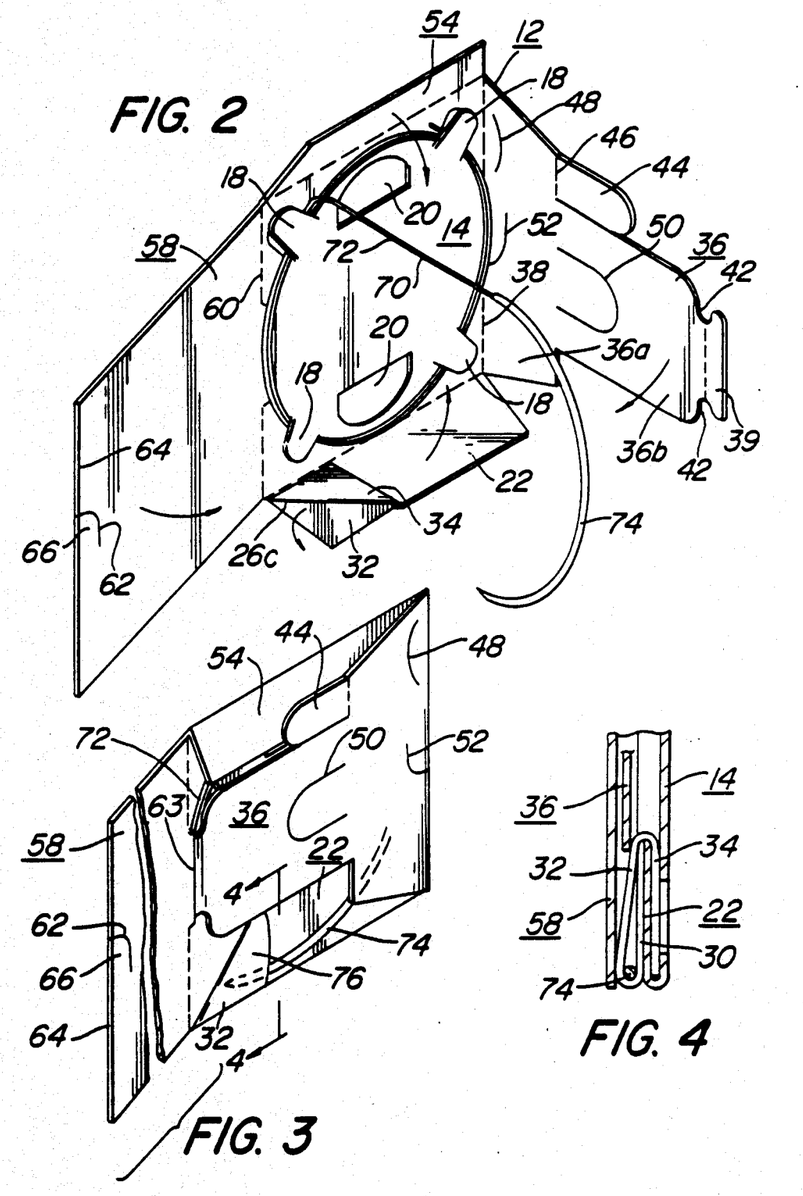
FIG. 2 is a perspective view showing the blank of FIG. 1 in a partially folded condition with a suture disposed thereon and showing the initial folding stages of the needle pocket.
FIG. 3 is a view similar to FIG. 2 with the needle point disposed in the needle pocket and the flaps other than the cover flap being shown in the folded position.
FIG. 4 is an enlarged sectional view taken along line 4—4 of FIG. 3.

A first flap 22 extending from the base panel 14 along the fold line 24 extends in its unfolded condition as viewed in FIG. 1 beyond the left hand edge of the base panel and is characterized by a plurality of fold lines 26a, 26b and 26c, each of which are respectively arranged at a 45° angle to the adjacent fold line and which have a common intersection at the left hand end 28 of the fold line 24. Fold line 26a is disposed at a 45° angle from the fold line 24, fold line 26b is disposed at 90° to the fold line 24, and fold line 26c is disposed at 135° angle to fold line 24. The fold lines 26a–c serve to form on the flap 22 a series of triangular flap portions 30, 32 and 34 of identical size. Flap portion 30 is formed between fold lines 26a and 26b, flap portion 32 between fold lines 26b and 26c, and flap portion 34 is formed outboard of the fold line 26c bounded by the outer end of the flap. The provision of the fold lines 26a–c in the particular arrangement described permits a number of folding arrangements of the left hand end of the flap 22, several of which arrangements provide different types of needle pockets as illustrated in FIGS. 2 and 5, for example, and described in detail herebelow.

Figures 7, 8:
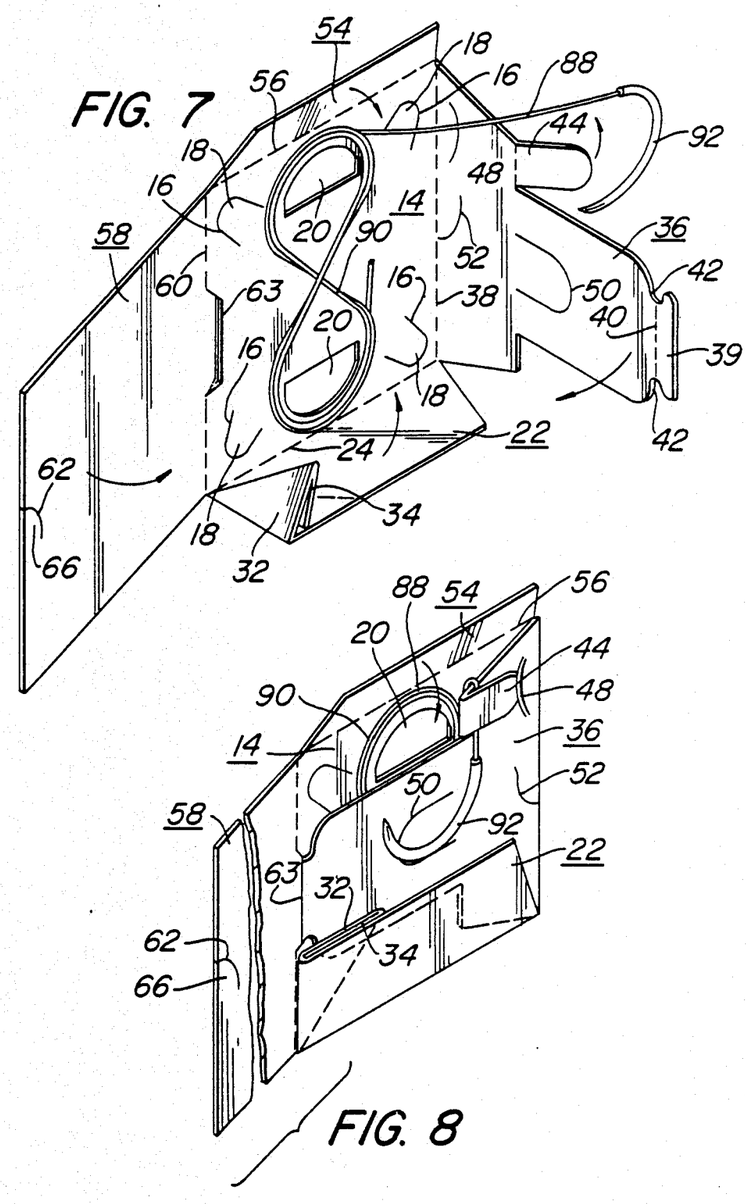
FIG. 7 is a view of the blank of FIG. 1 in a partially folded condition and shown with a suture disposed thereon with the thread thereof wound in a figure eight pattern.
FIG. 8 is a view similar to FIG. 7 with the flaps of the card shown folded except for the cover flap.

A second flap 36 extends from the base panel 14 along the fold line 38 perpendicular to the fold line 24. The second flap 36 includes an inner flap portion 36a extending from the fold line 38 and an outer portion 36b of a substantially narrower width extending outwardly to a narrow tab portion 39 defined by a fold line 40 extending across a necked down portion 42 of the flap. A secondary flap 44 extending from the fold line 46 on the flap portion 36a extends parallel to and adjacent the flap portion 36b and is adapted to cooperatively engage the curved slit 48 in its folded condition as illustrated in FIG. 8 and described hereinafter. The flap 36 further includes a central U-shaped slit 50 and a curved slit 52 extending from the fold line 38, the functions of which are described below.

A third flap 54 extending from the base panel 14 along a fold line 56 extends only a short distance outboard of the fold line 56 and is provided for the purpose of preventing outward egress of packaged thread as will be apparent from the following descriptions of the folded card embodiments.

A fourth or cover flap 58 extends from the base panel 14 along fold line 60 disposed opposite and parallel the fold line 38. The flap 58 is substantially the same size and shape as the base panel 14 so that, when folded along the fold line 60 after the inward folding of the panels 22, 36 and 54, the panel 58 will present a closed cover for the contents and flaps. A curved slit 62 intersecting the edge 64 of panel 58 opposite the fold line 60 forms a latching tab 66 which may be inserted into the slit 52 of the second panel 36 to fold the cover panel 58 in a closed position.

The fold line 66 is interrupted by a central offset slit 68 which, in the folded position of the cover flap 58 with respect to the base panel 14, provides an aperture within which the ends of the tab 39 of flap 36 may be engaged to secure the flap 36 in a folded position against the base panel 14 as shown for example in FIGS. 3, 6, 9 and 11.

The blank 12 may be utilized in a variety of folded card forms to accommodate various types of sutures and lengths of surgical thread. Four different usages of the blank of FIG. 1 are illustrated and described below to demonstrate the versatility of the present invention.

A first usage of the described blank is shown in FIGS. 2–4 wherein a suture 70 comprising a length of surgical thread 72 and a large curved needle 74 swedged thereto is to be packaged. In this instance, the thread portion of the suture 72 is wound in a clockwise manner around the tabs 18 and the flap 36 is closed over the winding. The needle is laid in superposed relation over the flap 36 with the point thereof disposed in a pocket 76 formed by the portions 30, 32 and 34 of flap 22 as shown in FIGS. 3 and 4. The pocket 76 is formed as follows: flap portions 32 and 34 are folded along fold line 26b as a unit so that fold line 26c overlaps fold line 26a. Flap portions 32 and 30 are then folded downwardly as a unit along the overlying fold lines 26c and 26a and the pocket 22 is thus formed between flap portion 30 and flap portion 32, the pocket being triangular in shape to provide a large opening for the needle point which is then directed toward the inner pocket corner.

With the pocket thus formed, the flap 22 is as illustrated folded over the base panel 14 and flap 36 and the needle end inserted into the pocket. The flap 54 is then similarly folded over panel 14 and flap 36. Finally, the cover flap 58 is folded and latched to cover the previously folded flaps.

For use of the package suture, the cover flap 58 and the flap 36 are opened to expose the needle 74 which is grasped and removed from the pocket 76. The flaps 22 and 54 are then opened to reveal the tabs 18 from which the thread may be unwound without kinking or knotting.

A further usage of the invention is shown in FIGS. 5, 6 and 6A wherein a suture 80 comprising a long straight needle 82 swedged to a length of thread 84 is packaged utilizing the card blank 12. For loading the card, the base panel 14 is placed over a pair of winding pins (not shown) which extend through the apertures 20, and the thread 84 is wound in a figure eight pattern on the base panel 14. With the needle 82 and a small adjacent portion of the thread 84 extending from the figure eight winding, the panel 36 is closed and latched by means of the tab 38 and slit 68. The flap 22 is then swung closed and the flap portions 32 and 34 thereof folded to form a triangular needle pocket 86 as shown in FIG. 6. To form this pocket, the flap portion 34 is first folded along fold line 26c beneath the flap portion 32, following which both these flap portions are folded along fold line 26b to overlie the flap portion 30, thus forming the pocket 86 between the flap portions 32 and 34, the pocket having an inwardly facing opening and serving to secure the needle in the diagonal position shown in FIG. 6. To complete the package, flaps 54 and 58 are folded closed and flap 58 is latched by means of the tab 66 and slit 52 as shown in FIG. 6A.

For use of the packaged suture as shown in FIGS. 5, 6 and 6A, the cover flap 58 is opened following which the needle 82 is removed from the needle pocket 86. The entire suture may then be freely drawn from the package for use.

Still another usage of the invention is shown in FIGS. 7 and 8 wherein the card 12 is utilized to package a suture 88 characterized by a length of thread 90 and a small curved needle 92. In a manner similar to that of FIGS. 5, 6 and 6A, base panel 14 is disposed on winding pins and the suture thread is wound around the pins in a figure eight pattern as illustrated. The card is then withdrawn from the pins and the flaps 36, 22, and 54 are folded over the suture thread to hold it in its figure eight configuration on the base panel 14. Prior to folding of the panel 22, the triangular portions 34 and 32 are sequentially folded along fold lines 26c and 26b in the manner shown in FIG. 8 so that they overlie the flap portion 30. The needle 92 and the suture thread 90 are folded over the flap 36 in a visible and accessible position. The secondary flap 44 is then folded along fold line 46 and latched into the slit 48 to anchor the suture thread in place closely adjacent the thread end of the needle. Finally, the cover flap 58 is closed and latched by means of the tab 66 and slit 52 to complete the card package.

For use, the opening of the package involves simply the opening of the cover flap 58, the removal of the needle from the slit 50 and the opening of the secondary flap 44, following which the suture thread is drawn from the interior of the package by an axial pulling of the suture.

Figures 9, 10:
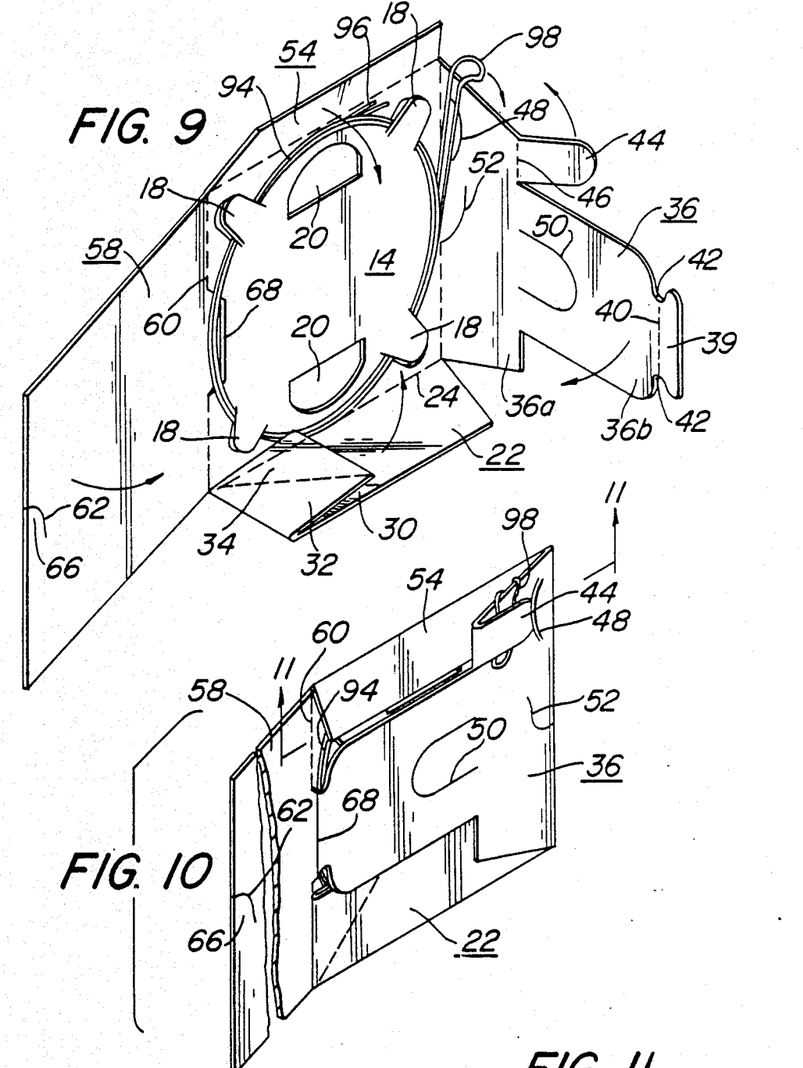
FIG. 9 is a perspective view showing the blank of FIG. 1 in a partially folded condition and with a length of suture thread wound thereon.
FIG. 10 is a view similar to FIG. 9 with the card flaps folded to cover and secure the thread but with the cover flap still open.
Figure 11:
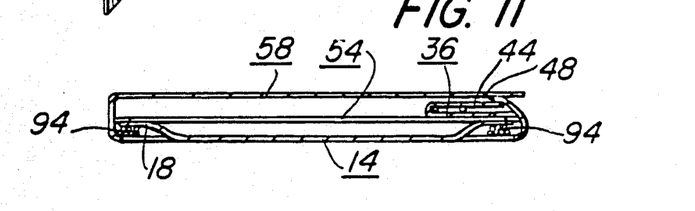
FIG. 11 is an enlarged sectional view taken along line 11—11 of FIG. 10.

In the usage illustrated in FIGS. 9-11, the blank 12 is employed to package a length of surgical thread 94. For this purpose, the tabs 18 are extended inwardly of the base panel 14 and the thread 94 is wound around the outstanding tabs. In the package illustrated, the ends 96 of the thread 94 are disposed in adjacent relationship, leaving a looped end 98 of the thread remaining as the winding is completed.

To close the card following the winding of the thread about the tabs 18, the triangular flap portions 32 and 34 of flap 22 are folded about fold lines 26b and 26c as shown in FIG. 9 into a flat relationship with the remainder of the flap. The flap 22 is then folded along fold line 24 over the adjacent portion of the wound thread 94 to prevent its movement in the direction of the flap. The flap 54 is then similarly folded over the base panel 14 to cover and secure the underlying portion of the thread 94.

Next, the flap 36 is folded as shown in FIG. 10 into an overlying relation with the base panel 14 and the flaps 22 and 54, with the looped portion 98 of the thread extending over the side edge of the flap and being secured in a visible, accessible position on the outer surface of flap 36 by the folding of tab 44 along fold line 46 into cooperative engagement with the slit 48.

Finally, as shown in FIG. 11, the cover flap 58 is folded into parallel relation with the base panel 14 to complete the card closure. The card may then be enclosed within one or more sterile outer covering packages in a manner well known in the packaging of surgical products.

The view of FIGS. 4 and 11 are schematically drawn for ease in identifying the various folded elements and would, in actuality, comprise a significantly thinner package than illustrated. The actual folded card thickness might be, for example, on the order of 1/16" with the larger dimensions measuring about $2\frac{1}{4} \times 2\frac{1}{2}$".

For use, the package illustrated in FIGS. 9-11 is opened by swinging the cover flap 58 into the position shown in FIG. 3 and releasing the tab 44 to free the looped end 98 of the thread. The flap 36 is then folded open as are the flaps 22 and 54 to permit the unwinding of the thread from the tabs 18 in an orderly, kink-free fashion.

Although its use is not illustrated, the central U-shaped slit 50 on flap 36 is useful to secure needles having their points engaging in the needle pocket, particularly straight needles of smaller size than that shown in FIGS. 5-6A. The flap formed by the slit 50 is extended outwardly from the flap 36 as needed and a needle slid in behind it to position the needle on the card.

Figures 12, 13, 14:
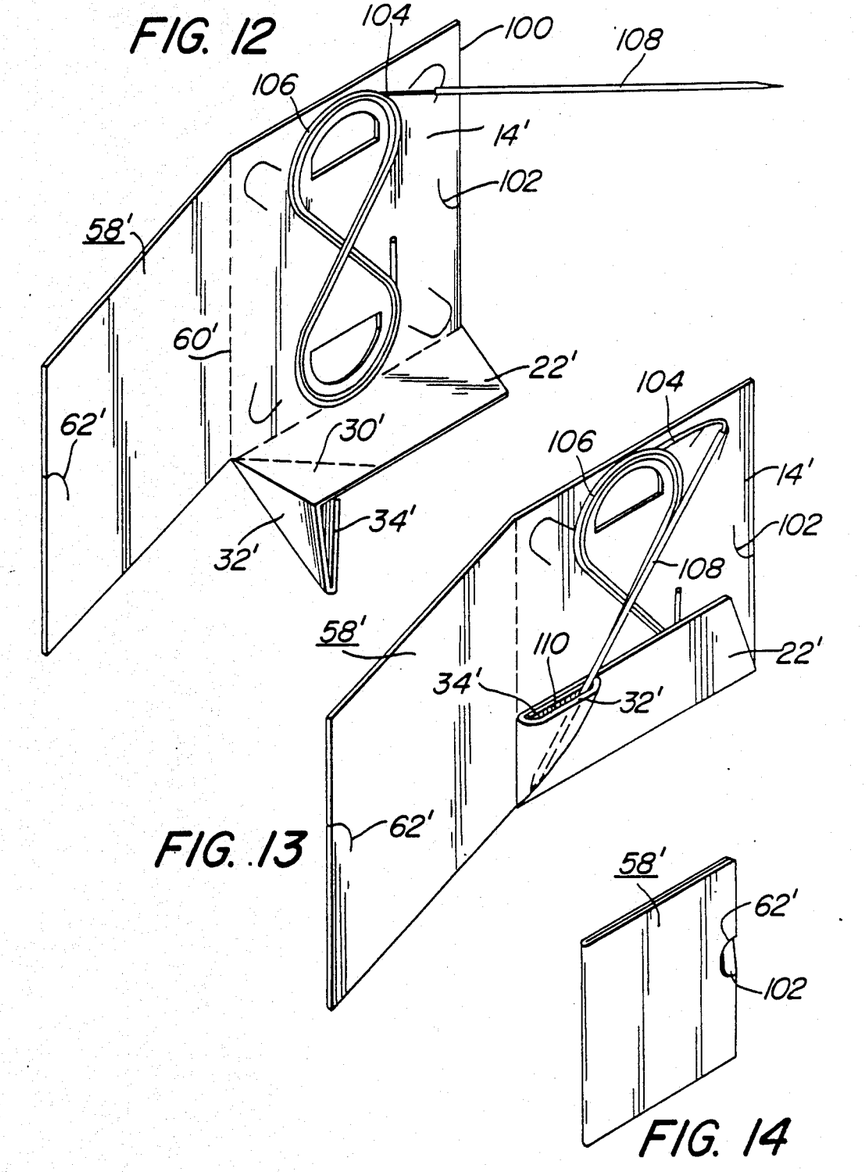
FIG. 12 is a perspective view of a modified form of blank shown in a partially folded condition with a suture disposed thereon.
FIG. 13 is a view similar to FIG. 12 with the first flap in a folded condition to form a needle packet.
FIG. 14 is a reduced view showing the package of FIGS. 12 and 13 with the cover flap closed.

In the embodiment of FIGS. 12-14, a card generally designated 100 similar to that of the previously described embodiment includes a base panel 14', a flap 22' and a cover flap 58' which are substantially identical to the corresponding elements of the previously described card. In the embodiment of FIGS. 12-14, the flaps 36 and 54 of the previous embodiment are omitted and the base panel 14' is modified in two respects: a slit 102 is provided to cooperate with the latching slit 62' of the panel 58', and in this embodiment, the base panel 14' does not include a slit 68 interrupting the cover fold line 60'.

In the utilization of the card shown in FIGS. 12-14, as shown in FIG. 12, a suture 104 comprising a length of thread 106 and a large straight needle 108 are packaged by configuring the thread in a figure eight pattern in the same manner as that shown in FIGS. 5 and 7. The flap 22' is then folded in the same manner as that of the embodiment of FIGS. 5-6A to form a needle pocket 110 as shown in FIG. 13. To complete the package, the cover 58' is folded over the flap 22' and secured in the closed position by interlocking the slits 62' and 102 as shown in FIG. 14. As with the previously described packages, the folded card may then be subsequently enclosed within one or more sterile covering packages in a well known manner.

Manifestly, changes in details of construction may be effected by those skilled in the art without departing from the present invention.

I claim:

1. A suture winding card comprising:
   a base panel for receiving a suture winding,
   at least one flap extending from an edge of said base panel and foldable over said base panel,
   said flap including a pocket on said flap,
   said pocket comprising three triangularly shaped foldable portions of said flap disposed in adjacent relation, said flap portions being defined by three fold lines each of which is disposed at a 45° angle to the adjacent fold line, said three fold lines intersecting at a common point at an edge of said flap, said foldable flap portions being selectively foldable to define a closed sided pocket having a pocket opening for receiving the end of a suture needle.

2. The invention as in claim 1 wherein the triangular flap portions are disposed at one end of said one flap.

3. The invention as claimed in claim 1, wherein a second flap foldably extends from said base panel adjacent said first one of said flaps, said second one of said flaps when folded over said base panel extending substantially across and substantially covering said base panel, and means for securing said second one of said flaps in a folded position overlying said base panel.

4. The invention as claimed in claim 3, wherein said second one of said flaps includes means for selectively securing a portion of a suture thread thereto on the exterior thereof when said flap is in a folded position.

5. The invention as claimed in claim 1, wherein said pocket portions are selectively foldable to dispose said pocket opening parallel to or perpendicular to said base panel edge.

6. A suture winding card comprising:
   a rectangular base panel for receiving a suture winding thereon,
   a plurality of flaps extending from edges of said base panel and foldable over said base panel to secure a suture thread coil disposed thereon,
   a first of said flaps including a plurality of triangularly shaped flap portions, said flap portions being selectively foldable to form a pocket for receiving the end of a suture needle,
   a second of said flaps disposed adjacent said first flap and extending in a folded position substantially across said base panel,
   a third of said flaps disposed opposite said first flap,
   and a fourth of said flaps disposed opposite second flap, said fourth flap being of the same size as said base panel and serving to cover said base panel and said folded first, second and third panels in its folded position.

7. The invention as claimed in claim 6, wherein said plurality of triangularly shaped flap portions of said first flap comprise three flap portions disposed in adjacent relation at one end of said first flap.

8. The invention as claimed in claim 7, wherein said three flap portions are defined by three fold lines each of which is disposed at a 45° angle to the adjacent one of said fold lines.

9. The invention as claimed in claim 8, wherein said three fold lines intersect at a common point on an edge of said first flap.

10. The invention as claimed in claim 6, wherein said second one of said flaps includes a secondary flap foldable with respect to said second flap, said secondary flap being engageable with a slit in said second flap to secure a portion of a suture thread on the exterior face of said second flap.

11. The invention as claimed in claim 6, including means for latching said fourth flap in a folded position to thereby secure said first, second and third flaps in a folded position.

12. The invention as claimed in claim 11, wherein said latching means comprises a tab on said fourth flap cooperating with a slit in said second flap.

13. A flat paper blank for folding into a suture winding card, said blank comprising;
   a rectangular base panel,
   a first edge of said base panel being defined by a fold line from which extends a first substantially rectangular flap,
   first, second and third angularly related converging pocket fold lines extending across said first flap and serving to define three triangularly shaped flap portions,
   a second edge of said base panel perpendicular to and adjoining said first edge and being defined by a fold line from which extends a second flap, said second flap having a dimension perpendicular to said latter fold line which is substantially equal to that of said base panel.

14. The invention as in claim 13, wherein the flap portions are substantially equal in size, each comprising a mirror image of the adjacent flap portion.

15. The invention as claimed in claims 12 or 13, wherein one of the pocket fold lines is colinear with the second edge.

16. The invention as claimed in claim 13, wherein the edge of said base panel opposite said first edge is defined by a third fold line parallel to said first fold line, and a third flap extending from said third fold line.

17. The invention as claimed in claim 16, wherein the panel edge opposite said second panel edge is defined by a fold line parallel with said second fold line, and a fourth flap extending from said fourth fold line, said fourth flap being of substantially the same size as said base panel.

18. The invention as claimed in claim 17, wherein one of the pocket fold lines is colinear with an edge of the base panel perpendicular to the first edge.

19. A suture winding card comprising:
   a base panel for receiving a suture winding,
   at least one flap extending from an edge of said base panel and foldable over said base panel,
   said flap including a pocket for receiving the end of a suture needle, said pocket being formed by three triangularly shaped flap portions disposed in adjacent relation and defined by three fold lines each of which is disposed at a 45° angle to the adjacent fold line,
   said three fold lines intersecting at a common point at an edge of said flap.

20. The invention as claimed in claim 19, wherein said triangular flap portions are disposed at one end of said flap.

21. A suture winding card comprising:
   a base panel for receiving a suture winding, at least one flap extending from an edge of said base panel and foldable over said base panel,
said flap including a pocket on said flap,
said pocket comprising three triangularly shaped foldable portions of said flap disposed in adjacent relation, said flap portions being defined by three fold lines intersecting at a common point at an edge of said flap, said foldable flap portions being selectively foldable to define a closed sided pocket having a pocket opening for receiving the end of a suture needle.

* * * * *